United States Patent

Hirano et al.

[11] Patent Number: 6,027,777
[45] Date of Patent: Feb. 22, 2000

[54] FORMING MATERIAL

[75] Inventors: Hiroyuki Hirano, Chiba; Wataru Okuyama, Tokyo; Nobuyasu Nakasugi, Kyoto; Shozo Oonishi, Chiba, all of Japan

[73] Assignees: Alcare Co. Ltd., Tokyo; SAN-APRO Limited, Kyoto, both of Japan

[21] Appl. No.: 08/728,843

[22] Filed: Oct. 10, 1996

[30] Foreign Application Priority Data

Feb. 21, 1996 [JP] Japan ...................................... 8-058499

[51] Int. Cl.⁷ .............................. A16L 15/10; A16L 15/14
[52] U.S. Cl. ...................... 428/35.4; 428/36.1; 428/36.5; 428/36.6; 428/68; 428/70; 428/71; 428/76; 428/137; 428/407
[58] Field of Search .................................. 428/68, 70, 71, 428/76, 137, 407, 35.4, 36.1, 36.5, 36.6

[56] References Cited

U.S. PATENT DOCUMENTS

| 4,683,877 | 8/1987 | Ersfeld et al. | 428/913 |
| 4,752,626 | 6/1988 | Hoye et al. | 521/175 |
| 5,480,376 | 1/1996 | Duback et al. | 428/68 |

FOREIGN PATENT DOCUMENTS

| 56-18325 | of 1981 | Japan . |
| 59-49013 | of 1984 | Japan . |
| 6-619978 A2 | 6/1994 | Japan . |
| 1543326 | of 1976 | United Kingdom . |

*Primary Examiner*—Elizabeth M. Cole
*Attorney, Agent, or Firm*—Haverstock, Garrett & Roberts

[57] ABSTRACT

A forming material for the fabrication of appliances for fixing, supporting, correcting and holding human bodies, characterized by a main forming material body including a quantity of granulated materials each coated with a moisture-curable urethane prepolymer contained within a water-permeable material container, the main forming material body being hermetically enclosed in a moisture-impermeable material container, wherein the moisture-curable urethane prepolymer and the water-permeable material container are unreactive with each other and have a low adhesive strength with respect to each other to provide good long term preservability and ease of operability to allow modeling and conforming the main forming material body to a desired shape.

5 Claims, 1 Drawing Sheet

FORMING MATERIAL

The present invention relates to a forming material for use in the fields of medical treatment, patient care and welfare, sports, etc. for contour or profile modeling parts of human bodies, which thus formed models can be used for the fixation, support, protection and correction of the human bodies, and, further, to a forming material for use in vehicles such as automobiles, airplanes, and other applications in which human bodies need to be fixed, that is, exactly positioned, supported and/or protected. More specifically, the present invention relates to a forming material useful for fixing and supporting human bodies on beds, chairs, inspection and examination devices, patient care and welfare devices, etc. without a sense of incongruity, and for the protection of human bodies.

BACKGROUND OF THE INVENTION

Various means are known in the fields of medical treatment, patient care and welfare for fixing-and supporting human bodies in a desired position on beds, chairs, inspection and examination devices and the like, which means can include, for instance, sandbags; foamed blocks; negative pressure type fixing devices, plastic foams; and sheet-shaped appliances. However, such known means generally lack sufficient fixing or exact positioning properties and supporting properties; and in cases where the patient moves after an initial fixation, such means must be set again or adjusted, and thus, the range of utility of such means is limited. For instance, examples of a sandbag or a foamed product used as a simple and handy means for temporarily fixing or supporting a human body onto a bed or an examination table are disclosed in Japanese Examined Patent Application Publication No. Sho 59-49013. However, such sandbags and foamed products lack sufficient fixing properties; and thus, a drawback thereof is that they are not suited for cases where the human body must be fixed accurately or for application requiring long period of fixing or reproducibility of a previously fixed position. A negative pressure type fixing appliance, that is, an airtight bag containing foamed granulated materials, which bag is adapted in such a manner that, by evacuating the interior of the bag by means of a vacuum pump, fixing properties are imparted to the bag, is typically used in such a manner that, first, it is laid down on a bed, an inspection stand, an examination table, or a chair in a state filled up with air, and then a human body is placed on the appliance, which is then evacuated by means of a vacuum pump, whereby the shape of the human body is formed or modeled, for example, as disclosed in Japanese Examined Utility Model Application Publication No. Sho 56-18325. Such a negative type fixing appliance is convenient for temporarily fixing or supporting a large portion of a human body, but it does not possess long-term fixing properties or reproducibility, and, in addition, a large-sized vacuum pump must be used. Therefore, such a negative type fixing appliance has the drawback that it is generally best suited to be utilized only in special limited applications. Plastic foams and sheet-shaped fixing appliances are typically used in such a manner that the foam or sheet-shaped appliance is mounted on a part of a human body so as to fix, support, protect or correct the part of the human body by itself; and therefore, such plastic foams and sheet-shaped fixing appliances are light in weight but not well compatible with the living body, and various kinds or types thereof must be prepared in advance. These are drawbacks of such plastic foams and sheet-shaped fixing appliances. Furthermore, in the case where such plastic foams and sheet-shaped fixing appliances are fabricated so as to satisfy the specific requirement or condition in an individual case in order to secure a compatibility with a living body, a shortcoming arises with respect to the expense and time required for the manufacture thereof.

As an example of the case where supporting accuracy and/or reproducibility are required, there can be pointed out the case of treatment of cancers in the field of medical treatment. As one treating method therefor, radiation therapy is point out. As the types of cancers which can be healed by radiation therapy alone, there can be pointed out cancer of the head-neck, cancer of the cervix, cancer of the prostate, lymphogranuloma, cancer of the lungs, cancer of the esophagus, cancer of the bile duct, etc. In order to locally control or suppress such a tumor without the occurrence of a radiation hazard, the radiation treatment must be carried out in a very narrow dosimetric range. However, the control or suppression probability of tumors is conspicuously increased by increasing the dose of radiation. Thus, in order to control or suppress a tumor without the occurrence of a lesion or trouble in the normal tissues, it is important to determine an accurate exposure position and employ a well contrived exposure method; that is, how to concentrate the radiation dose on the tumor portion is important. To this end, it becomes necessary to perform exposure from two or more directions, and how to fix the patient's body so as to reduce the movement thereof is important. For that, treatments have so far been performed in such manner that a mark is put on the body surface of a patient using a marking ink or the like so as to allow positioning and aiming the radiation apparatus to emit its radiation onto the affected part accurately. With this method, however, a high-level of skill is required for the manipulation of the apparatus, and, further, it takes time to perform the positional adjustment. In addition, there is the further problem that, during exposure, the portion of the patient's body to be exposed to the radiation may be shifted due to the movement of the patient. Thus, for keeping the patient's body fixed, there have been practiced various methods such as the method according to which the contour or profile of the patient's body is modeled with a gypsum to make a negative model; from this negative model, a positive model is developed; in conformity with the thus made positive model, a shell is fabricated with a PVC resin, with which the patient's body is fixed, and the method according to which a plate made of a thermoplastic resin is softened to make a body-fixing shell directly from the patient's body, by use of which shell the patient's body is fixed. These methods are all of the type in which a fixing appliance is put over the patient from above to fix his or her body; and thus, since the patient is fixed only from the upper surface of his or her body, these methods are insufficient for the purpose of fixing the patient's whole body including the lower surface thereof. In addition, considerable time and skill are required for the fabrication of the required positive model. Further, the high-energy X-rays used have surface buildup characteristics such that the absorbed dose of high-energy X-rays gradually increases from the surface portion to the deeper portion, and, at a depth of several mm to several tens of millimeters (mm), the absorbed dose thereof reaches its peak value, and, the use of a PVC resin or a thermoplastic resin which has a high degree of radiation absorption has been found to result in increasing the body surface dose of the patient, thus causing radiation hazards such as dermatitis, etc. Therefore, it is important to use a material having a small radiation absorption as the material of the fixing appliance used in radiation therapy. Further, in radiation therapy, the exposure amount per one radiation dose is typically set at a small value in order to prevent the occurrence of an adverse reaction; and thus, the required exposure is made by dividing it into several tens of times, ranging over a period of several months. Due to this, the deformation, the breakage, the ease in preservation, the weight at the time of movement, etc. of the fixing appliances are important problems or factors. Additionally, a fixing appliance made of a PVC resin or a thermoplastic resin is liable to be deformed during normal storage and use and thus may not provide a sufficient fixation.

In the case of some physically handicapped persons, parts of their bodies are deformed to such a degree that it is difficult for them to sit on ordinary chairs, due to which, at present, supporting appliances fitted to the bodies of physically handicapped persons are made by modeling the contours or profiles of such physically handicapped persons' bodies repeatedly many times by the use of a gypsum or a resin. The problem with this method is that a number of steps and days are required for obtaining the finally finished supporting appliance, and in addition, a high level of fitting and manufacturing skill is required, and the manufacturing costs are high.

As the percentage of the population playing sports is increasing, the number of people who suffer injuries due to sports is also increasing. In particular, due to the fact that sports are professionalized, the contact in sporting competitions has become increasingly severe, as a result of which players and athletes tend to get injured more and more; and thus, for prevention of such injuries and for protection of the injured parts of players and athletes, various appliances are proposed. The appliances in this field are required to be light in weight and shock-resistant, so that it is necessary to make the appliances by the use of special material so as to accurately fit to the injured or protected parts of persons wearing these appliances. For that, the troublesome steps of making models and adjustment thereof are required, so that the manufacturing costs are high. If, in order to avoid such troublesome steps, a number of types of standard appliances are prepared in advance so that a user can select the most suitable one from among them, then it is costwise advantageous, but the selected appliance is not necessarily one perfectly suited to the user; and thus, the function of making an appropriate prevention or the function of protection cannot be fulfilled.

In the fields of automobiles, airplanes and other vehicles, the seats in vehicles required to have high speed or mobility are formed so that the bodies of the drivers can be tightly supported on the seats, and therefore, there arises the drawback that, in respect of the material, shape and fine adjustment mechanism of the seats, high-grade design techniques are required, which results in high manufacturing costs.

OBJECTS OF THE INVENTION

It is therefore a principal object of the present invention to provide a forming material that can be easily formed and which can be used with various appliances and equipment used in various fields as mentioned above for the fixation, support, correction, protection, etc. of human bodies.

SUMMARY OF THE INVENTION

In order to achieve the above-mentioned object, the forming material according to the present invention is composed in such a manner that a predetermined amount of granulated or similar materials each coated with a moisture-curable urethane prepolymer are wrapped up in or otherwise contained within a water-permeable material container having openings smaller than the size of the granulated or similar materials, and the thus obtained forming material is hermetically enclosed in a moisture-impermeable material container or vessel.

As the water-permeable material, there is preferred a material which is unreactive with the moisture-curable urethane prepolymer and stands in such a relationship to the granulated materials coated with the moisture-curable urethane prepolymer that the adhesive force between the granulated materials and the water-permeable material is low, the adhesive force being preferably about 0.5 kilograms force (kgf)/25 millimeters (mm) or less.

Preferred as the water-permeable material is a knitted fabric, a woven fabric, a non-woven fabric formed by yarns comprising a fiber aggregate or a mesh-like material comprising monofilaments, the fabrics and the mesh-like material being unreactive with the moisture-curable urethane prepolymer.

Further, it is preferred that the water-permeable material have an elongation capability of about 15% or greater in at least one direction so as to be at least somewhat highly deformable.

The preferred moisture-curable urethane prepolymer is a urethane prepolymer comprising a polyisocyanate and a polyol. A catalyst compounded into the moisture curable urethane prepolymer in such an amount that the curing time may become from about 2 to about 30 minutes is advantageous, and further, a thixotropic agent added to the moisture-curable urethane prepolymer is also advantageous.

According to the present invention, it is preferable to ensure that the granulated materials with their surfaces covered by a moisture-curable polyurethane prepolymer are put, or wrapped, in a predetermined amount in conformity with the appliance or equipment to be formed, into a bag-like container composed of a water-permeable material and to keep the bag in a moisture-impermeable container or vessel in a hermetically sealed state until the forming material is put to actual use.

The water-permeable material wrapping up or containing the granulated materials therein facilitates putting together the predetermined amount of granulated materials coated with a moisture-curable urethane prepolymer into one mass and isolating the granulated materials so that the operator and the appliance wearer or user can handle the forming material without directly touching the urethane prepolymer to thereby avoid the adverse effect on their skin by the resin and also to facilitate the operation. Since it is desired that the water-permeable material is unreactive with the resin and the resin is a moisture-curable urethane prepolymer, the water-permeable material should be a material which has a low water content; that is, a material which does not contain a material or substance having a chemical structure which activates the reactive group of the urethane prepolymer. As for the size, shape and structural properties of the water-permeable material container, it is important, in improving the maneuverability or operability, to select a water permeable container having properties in conformity with the appliance or equipment to which the forming material is applied. For instance, the shape of the water-permeable material should be selected in conformity with the application or equipment which is to be formed with the forming material, and, in the case where the size of the water-permeable material container is to be large, it adds to convenience to divide the interior of the container composed of the water-permeable material into several individual chambers.

DETAILED DESCRIPTION OF THE PREFERRED EMBODIMENTS

Composition

As the water-permeable material of the present invention, there can be used, for instance, synthetic fibers such as polyester (PET), polypropylene (PP), polyethylene (PE), polyacryl, polyurethane, styrene/isoprene/styrene copolymer (SIS), polyamide, etc., regenerated fibers or natural fibers such as staple fiber, rayon, cotton, hemp, etc., inorganic fibers such as glass fibers etc., but those fibers which are reactive with the moisture-curable urethane prepolymer or high in water content must have their surfaces treated to become unreactive with the urethane prepolymer or must be dried up to have the water content thereof removed. As preferred materials, there are pointed out polyester, polypropylene, polyethylene, polyurethane, and SIS which need not be subjected to the above-mentioned treatment. Particularly advantageous fibers are those fibers obtained by mix spinning polyester having thermal sealing properties with one of polypropylene, polyethylene and SIS and fibers made of one of polypropylene, polyethylene, polyurethane and SIS or mix spinning fibers composed thereof.

As for the finished state of the water permeable material, there are pointed out as examples a knitted fabric, a woven fabric, a non-woven fabric and a fabric of a net or net-like structure. A preferred finished state is that of a knitted fabric or a non-woven fabric which has a flexibility and a stretchability sufficient to allow the fabric to get to fit the irregularities of the appliance or equipment or the part of a person to which the forming material is applied. To obtain such flexibility and stretchability, the fabric used preferably should have an elongation of about 15% or greater in at least one of the lengthwise and breadthwise directions. If the elongation is less than the above-mentioned numerical value, it will be more difficult to model.

As the water-permeable material, a material which has a low affinity with the moisture-curable urethane prepolymer must be selected in view of the fact that this material is used together with the granulated materials coated with a polyurethane prepolymer. As an index therefor, it is pointed out that the adhesive force acting between the granulated materials coated with the moisture-curable urethane prepolymer and the water-permeable material should be about 0.5 kgf/25 mm or less as measured by an adhesive force measurement conformed to the JIS Z0237.8 standard for stickiness. If the adhesive strength is greater than such numerical value, the urethane prepolymer and the water-permeable material will be brought into one integral body during a long-period preservation of the forming material, so that the forming material will become unusable. To additionally take operability into consideration, the adhesive strength should preferably be about 0.3 kgf/25 mm or less, and more preferably about 0.1 kgf/25 mm or less.

Particularly, in the case where the yarns used in the knitted fabric, woven fabric or the like comprise aggregates of a large number of thin fibers, it is desirable to make a treatment for lowering the affinity of the water-permeable material with the moisture-curable urethane prepolymer so as to ensure that the moisture-curable urethane prepolymer can not penetrate into the spaces or clearances between the fibers. As the agent used for the above-mentioned treatment, a fluorine series, a paraffin series, an alkyl chromic chloride series, an alkylmethylpyridinium chloride series, an alkylethylene urea series substance, or the like can be used. The preferred amount of the treating agent used for such treatment is such that from about 0.1 to about 6% of the effective component thereof can attach, and, as for the treating method, the knitted fabric or woven fabric used may be impregnated with the treating agent, or the treating agent may be applied to or sprayed on the fabric before or after the production or formation of the fabric.

Preferable as the water-permeable material is a knitted fabric comprising yarns, about 300 deniers, made of one or a combination of polypropylene and polyester, the knitted fabric being finished in a tube-like shape with about 22 yarn/inch in the courses direction and about 22 yarns/inch in the wales direction, and having a weight per unit area of about 230 g/m$^2$. The knitted fabric should also have an extensibility or elongation of from about 5 to about 60% in the lengthwise direction and from about 50 to about 300% in the breadthwise direction. As such a knitted fabric, there is, for instance, a product available on the market under the trade name of "WHITE NET" (manufactured and sold by Alcare Co., Ltd.). By treating the water-permeable material with a treating agent comprising a fluorine series emulsion so as to obtain an effective treating amount of about 0.7%, the storage stability is enhanced, and the operability is improved.

The granulated materials should be composed of a material unreactive with the polyurethane resin and since the resin is moisture-curable, the granulated material must be low in water content. As materials usable for the granulated materials, there are organic and inorganic materials. As the organic materials, there are pointed out single polymers or copolymers of polyethylene, polypropylene, ethylene vinyl acetate copolymer, polystyrene, polyurethane, ABS resin, polyvinyl chloride resin, polyvinylidene chloride resin, polyacrylate, silicone resin, etc. and high-molecular weight compounds such as cellulose acetate, cellulose, rubber, etc., while, as the inorganic materials, there are pointed out porous or expandable materials such as calcined perlite, silas balloon, porous glass, hollow glass, slag, pumice, etc.; the surfaces of these materials may be coated to obdurate the pores in the surfaces thereof. The above-mentioned materials can be used each alone or in a combination of two or more thereof.

As for the specific gravity of the granulated materials used, if the specific gravity is high, there arises the drawback that, in the case of using the forming material in radiation therapy, the exposed dose of the human body differs between the portion of the radiation which has passed through the granulated materials and the portion which has not passed through the granulated materials due to the radiation absorption of the granulated materials, and further, if the specific gravity of the granulated materials is high, the weight thereof is increased accordingly, so that the handling of the forming material becomes more difficult. Thus, the preferred apparent specific gravity of the granulated materials is about 1.50 or below and should desirably be from about 0.0125 to about 1.00 in practical use. Further, as for the size of the granulated materials, it should be noted that, if they are too large in size, it becomes hard to make the surfaces of the forming material flat and to obtain good modeling properties. Conversely if the granulated materials are too small in size, they become dense, as a result of which the hydro-extraction, air permeability and lightweight properties of the forming material are deteriorated. As for the diameter of the granulated materials, it should desirably be from about 0.05 to about 10 mm and, and preferably, from about 0.5 to about 5 mm.

As for the structure of the granulated materials, they may be solid or hollow or may comprise a foamed material. As for the shape thereof, they can be of any shape but are preferably spherical and hollow or comprise a foamed material. If they are spherical in shape, an advantage is that they can be arranged in good order, giving the impression of being uniform; a uniform air permeability can be obtained; water can be well drained off them; the points of contact between them are disposed in good order; and a uniform strength can be realized. Furthermore, the finished product possesses cushioning properties.

As the moisture-curable urethane prepolymer coated on the granulated materials, there can be used, for instance, an isocyanate group-terminated prepolymer which is obtained by reacting a polyol with a polyisocyanate. As the polyol, there can be used a low-molecular weight polyol (such as for instance polyethylene glycol, polypropylene glycol, glycerin, or the like); or a polyether polyol which is obtained by adding an alkylene oxide (such as for instance ethylene oxide, propylene oxide or the like) to a polyphenol; a polyester polyol which is obtained by the dehydration condensation reaction between a low-molecular weight polyol and a dicarboxylic acid (such as for instance adipic acid, phthalic acid or the like); a polylactone polyol which results from the ring-opening-polymerication of a lactone group (such as for instance γ-butyl lactone, ε-caprolactone or the like); a polytetramethylene glycol resulting from the ring-opening-polymerization of a tetrahydrofuran; castor oil or the alkylene oxide addition product thereof; a hydroxyl group-terminated polydien polyol which is a polymer of a diene compound such as butadiene, isoprene or the like, or the hydrogenated substance thereof or the like. These can be used each alone or in a combination of two or more thereof.

As the polyisocyanate, there can be used, for instance, an aromatic polyisocyanate such as 2,4-tolylene diisocyanate, 2,6-tolylene diisocyanate, 4,4'-diphenylmethane diisocyanate, 2, 4'-diphenylmethane diisocyanate, p-phenylene diisocyanate, polymethylene polyphenylene polyisocyanate or the like; an aliphatic polyisocyanate such as hexamethylene diisocyanate or the like, a cycloaliphatic polyisocyanate such as 3-isocyanatemethyl-3,5,5-trimethylcyclohexyl isocyanate or the like; an aryl aliphatic polyisocyanate such as xylene disisocyanate or the like; and a carbodiimide modified or isocyanate modified polyisocyanate or the like; and these substances may be used each alone or in a combination of two or more thereof. Desirable ones of these substances are aromatic polyisocyanates such as 4,4'-diphenylmethane diisocyanate, 2, 4'-diphenylmethane diisocyanate, p-phenylene diisocyanate and polymethylene polyphenylene polyisocyanate, and the carbodiimide modified polyisocyanates thereof.

The compounding ratio between the polyol and the polyisocyanate for obtaining an isocyanate group-terminated urethane prepolymer is normally from about 1.2 to about 10 equivalents of the polyisocyanate per 1 equivalent of the polyol and, preferably from about 1.5 to about 5.0 equivalents of the polyisocyanate per 1 equivalent of the polyol. Further, this reaction is normally achieved by stirring the reactants under heating at from about 30 to about 120° C. The viscosity of the urethane prepolymer thus obtained is normally from about 10 to about 2000 P and, preferably from about 50 to about 1000 P as measured at 20° C. The amount of this urethane prepolymer for coating the granulated materials is preferably from about 2 to about 30 volume % and, more preferably from about 10 to about 30 volume %, based on the granulated materials. If the coating amount is less than about 2 volume %, it has been found that the granulated materials cannot be hardened to a sufficient strength. If the coating amount exceeds about 30 volume %, sufficient clearances cannot be achieved between the adjacent granulated materials, so that there is no way for the carbon dioxide gas produced when the urethane prepolymer is cured with moisture to escape, as a result of which the forming material can become swollen, and thus, there arises the possibility that an accurate modeling cannot be performed. Further, during the storage or preservation of the forming material, the moisture-curable urethane prepolymer has been found to flow from the granulated materials, migrate downwardly, and thus, a uniformly formed product cannot be obtained.

The addition of a thixotropic agent to the moisture-curable urethane prepolymer is desirable as it prevents the uneven disposition of the resin and the penetration of the resin into the wrapping material during the manufacture and preservation of the forming material. As inorganic thixotropic agents, there are pointed out silica, titanium oxide and zinc oxide, while as organic thixotropic agents, the following are pointed out by way of example: polyalkylene modified compounds which are each obtained, for instance, by treating the terminal hydroxyl group pf a polyalkylene glycol with a hydroxyl group treating agent, such as for instance the organic thixotropic agents each obtained, by treating polyethylene glycol, polypropylene glycol or a copolymer thereof with methyl chloride, an aliphatic acid or the like; aromatic carboxylates such as for instance n-butyl benzoate, n-stearyl benzoate, methyl n-butyl phthalate, methyl n-stearyl phthalate, ethyl isodecyl phthalate, ethyl n-stearyl phthalate, 2-ethylhexyl n-stearyl phthalate, 1,2 di-n-butyl n-stearyl trimellitate, n-butyl-n-stearyl phthalate, 1,2 di-n-butyl n-stearyl hemimellitate, 1,3 di-n-butyl n-stearyl trimesate, n-butyl n-stearyl phthalate, n-amyl lauryl phthalate, 2-ethyl hexyl lauryl phthalate; and benzylidene sorbital, ditolylidene sorbitol, etc. which are synthesized by the acetalizing reaction between D-sorbitol and aromatic aldehide. The compound synthesized by the reaction between D-sorbitol and aromatic aldehide is particularly advantageous. The amount of employment of such a compound varies depending on the composition of the moisture-curable urethane prepolymer, the addition of a catalyst, a stabilizer, etc., and the kind and amount of the inorganic thixotropic agent, but the addition amount thereof is from about 0.01 to about 6.00 wt % and, preferably from about 0.5 to about 3.0 wt %, based on the urethane prepolymer.

To the moisture-curable urethane prepolymer, a suitable catalyst, a suitable stabilizer, a suitable anti-foaming agent, a suitable anti-oxidizing agent, a suitable coloring agent, a suitable filler, etc. can be further added. As the catalyst, for instance an ethyl ether group catalyst can be pointed out; and to improve storage stability, an ethyl ether group amine catalyst is desirable. As the amine catalyst, for instance bis (dimethylaminoethyl) ether, bis (morpholino ethyl) ether, bis 2,6 (dimethyl morpholinoethyl) diethyl ether, or the like can be pointed out. These substances can be used each alone or in a combination of two or more thereof. Though the amount of the catalyst used can vary with the type of catalyst, the amount of the catalyst is preferably from about 0.01 to about 5 wt % based on the urethane prepolymer; and it is preferred to adjust the amount of catalyst used so that the modeling material may be cured in from about 2 to about 30 minutes.

Usable as the stabilizer is an acidic substance such as an organic acid, organic acid chloride, acidic phosphate ester or the like, a chelating agent (a diketone compound, hydroxycarboxylic acid) or the like. Though the particularly desirable ones of these substances are determined depending on their relationship with the urethane prepolymer, the catalyst, etc., methane sulfonic acid which is an organic acid is preferable. The amount of employment of the stabilizer is preferably from about 0.01 to about 2 wt % based on the urethane prepolymer.

As the anti-foaming agent, there can be pointed out a silicone series anti-foaming agent and a wax series anti-foaming agent, of which a silicone series anti-forming agent is preferable. The amount of anti-foaming agent used should desirably be from about 0.01 to about 1 wt % based on the urethane prepolymer.

Usable as the anti-oxidizing agent, for instance, is a hindered phenol, and a phosphorus system compound, a hindered amine, and a sulfur system compound. A preferred anti-oxidizing agent is a tetrakis (methylene-3'-(3',5' di-tertiary-butyl-4-hydroxyphenyl) propionate) methane. The amount of the anti-oxidizing agent used should desirably be from about 0.01 to about 1 wt % based on the urethane prepolymer.

As the coloring agent, an official coloring matter which is less liable to cause dermatitis is preferably utilized. Further, as the filler, an inorganic system and an organic system powdery substance can be utilized. For instance, silica, titanium oxide, zinc oxide, or the like can be utilized.

Several Embodiments of the present invention will now be described.

Manufacture of the Moisture-Curable Urethane Prepolymer Composition

Into a four-neck flask, 650 g of PPG-2000 (polypropylene ether glycol with a hydroxyl number of 56 mg-KOH/g, manufactured by Sanyo Chemical Industries, Ltd.) was put as a polyol component and vacuum-dehydrated under heating, and thereafter, to the thus treated polyol component, 321 g of ISONATE 125M (4, 4'-diphenylmethane diisocyanate, manufactured by Mitsubishi Chemical-Dow Corporation) was added as a polyisocyanate component and stirred at 60° C. After the reactants were reacted further for three hours, 20 g of bis (dimethylmorpholinoethyl) ether as a catalyst and 0.6 g of methane sulfonic acid as a stabilizer were added at 50° C. and stirred and mixed for one further hour, whereby a moisture-curable urethane prepolymer composition identified by the letter A was obtained. The viscosity of this composition was 60 P at 20° C., and the curing time thereof was 8 minutes. In similar manners, moisture-curable urethane prepolymer compositions identified by the letters B, C and D which differed in compounding ratios from each other were synthesized as shown in Table 1. Further, as comparative example, two moisture curable urethane prepolymers identified by the letters E and F were synthesized as shown in Table 2.

TABLE 1

(Formulation of moisture-curable urethane prepolymer compositions)

| Names of compositions | Poliol component g | | Polyisocyannate component g | | Catalyst g | | Stabilizer g | | Other compounding agents g | | Viscosity P | Curing time min. |
|---|---|---|---|---|---|---|---|---|---|---|---|---|
| A | PPG-2000 | 657 | ISONATE 125M | 321 | Bis(2,6-dimethylmorpholino)diethylether | 20 | Methane sulfonic acid | 0.6 | | | 60 | 8 |
| B | PPG-2000 PPG-400 | 441 150 | ISONATE 125M | 386 | Bis(2,6-dimethylmorpholino)diethylether | 20 | Methane sulfonic acid | 0.6 | | | 330 | 5 |
| C | PPG-2000 PPG-400 | 323 231 | ISONATE 125M | 423 | Bis(2,6-dimethylmorpholino)diethylether | 20 | Methane sulfonic acid | 0.6 | | | 1200 | 6 |
| D | PPG-2000 | 657 | ISONATE 125M | 321 | Bis(2,6-dimethylmorpholino)diethylether | 20 | Methane sulfonic acid | 0.6 | Thixotropic agent | 0.4 | 250 | 4 |

*PPG-2000: Polypropylene ether glycol, hydroxyl number 56 mg-KOH/g, manufactured by Sanyo Chemical Industries, Ltd.
*PPG-400: Polypropylene ether glycol, hydroxy number −277 mg-KOH/g, manufactured by Sanyo Chemical Industries, Ltd.
*ISONATE 125M: 4,4-diphenylmethane diisocyanate, manufactured by Mitsubishi Chemical - Dow Corporation
*Thixotropic agent: Gelol-D, manufactured by New Japan Chemical Co., Ltd.

TABLE 2

(Formulation of moisture-curable urethane prepolymer compositions)

| Names of compositions | Poliol component g | Polyisocyannate component g | Catalyst g | Stabilizer g | Other compounding agents g | Viscosity P | Curing time min. |
|---|---|---|---|---|---|---|---|
| E | PPG-2000 542 | ISONATE 125M 453 | Bis(2,6-dimethylmorpholino)diethylether 20 | Methane sulfonic acid 0.6 | | 5 | 4 |

TABLE 2-continued (Formulation of moisture-curable urethane prepolymer compositions)

| Names of com- positions | Poliol component g | | Polyisocyannate component g | | Catalyst g | | Stabilizer g | | Other compounding agents g | Viscosity P | Curing time min. |
|---|---|---|---|---|---|---|---|---|---|---|---|
| F | PPG-2000 PPG-400 | 256 277 | ISONATE 125M | 444 | Bis(2,6-dimethylmor- pholino)diethylether | 20 | Methane sulfonic acid | 0.6 | | 3000 | 5 |

*PPG-2000: Polypropylene ether glycol, hydroxyl number 56 mg-KOH/g, manufactured by Sanyo Chemical Industries, Ltd.
*PPG-400: Polypropylene ether glycol, hydroxy number - 277 mg-KOH/g, manufactured by Sanyo Chemical Industries, Ltd.
*ISONATE 125M: 4,4-diphenylmethane diisocyanate, manufactured by Mitsubishi Chemical - Dow Corporation Application of the Moisture-Curable Urethane Prepolymer to the Granulated Materials Three batches, each containing 2.26 liters of foamed polystyrene beads (identified as Granulated Materials 1) with a specific gravity of 0.03, commercially available under the trade name Eslen Beads HE manufactured by Sekisui Plastics Co., Ltd., comprised of grains each having a diameter of about 1.6 mm, were put respectively into kneaders, and 142.8 g of each of the moisture-curable urethane prepolymers A, B and C was made to thoroughly attach respectively to a batch of the foamed polystyrene beads under agitation in a nitrogen atmosphere. Similarly, two kinds of granulated materials, that is, foamed polystyrene beads (Granulated Materials 2) having a specific gravity of 0.14, commercially available under the trade name by Eslen Beads HE, manufactured by Sekisui Plastics Co., Ltd., each having a diameter of about 0.8 mm, and foamed polyvinyl chloride beads (Granulated Materials 3) having a specific gravity of 1.4 and each having a diameter of about 0.2 mm, were prepared as different granulated materials, 2.26 liters of each of these two kinds of particulate bodies were put into kneaders, and 142.8 g of the moisture-curable urethane prepolymer composition B was made to thoroughly attach to each of said Granulated Materials 2 and 3 under agitation in a nitrogen atmosphere.

Manufacture of Specimens to be Preserved

Next, the respective water-permeable materials shown in Table 3 were each formed into a bag having a size of 20 cm×30 cm; and, into the thus formed bags, the granulated materials onto which the above-mentioned various kinds of moisture-curable urethane prepolymer compositions were made to attach, respectively, were placed, and the mouths of the bags were sealed up, with which the main forming material bodies according to the present invention were obtained. These main forming material bodies were each put into aluminum-laminated plastic bags of three layered construction having layers of polyethylene-aluminium-polyethylene as a moisture-impermeable material container; and then these bags were heat-sealed, thus forming specimens to be preserved, as shown in Table 4, whereafter the curing, the penetration into the water-permeable material of the moisture-curable urethane prepolymer composition, and the run-off of the moisture-curable urethane prepolymer composition from the water-permeable material, etc. were evaluated. The results of the evaluation are shown in Table 4.

TABLE 3

(Water-permeable materials)

| Kind | Material | | Thickness of yarns | Density | Structure | Openings (maximum) mm | Elongation |
|---|---|---|---|---|---|---|---|
| White net | PP PET | 75% 25% | 300D | Warp: 22 yarns/inch Weft: 22 yarns/inc | Knitting | 1.1 | Warp: 18% Weft: 250% |
| Non-woven fabric of polyester | PET | 100% | | 40 g/m$^2$ | Spunlace | 0 | Warp: 42% Weft: 100% |
| Stockinet | Cotton | 100% | 300D | Warp: 22 yarns/inch Weft: 22 yarns/inc | Knitting | 1.1 | Warp: 15% Weft: 350% |
| White net II | PET Spandex ® | 95% 5% | 300D 70D | Warp: 10 yarns/inch Weft: 10 yarns/inc | Knitting | 1.5 | Warp: 18% Weft: 250% |

TABLE 4

(Embodiments & Comparative Examples)

| | No. | Conditions Moisture-curable urethane prepolymers | Granulated materials | Water-permeable material | kgf/25 mm Adhesive strength | Evaluation Storage stability Curing state | Penetration state | Usability |
|---|---|---|---|---|---|---|---|---|
| Embodi- | 1 | A | 1 | White net | 0.1 | ○ | Δ | Usable |
| ments | 2 | B | 1 | White net | 0.1 | ○ | ○ | Good to use |
| | 3 | C | 1 | White net | 0.1 | ○ | ○ | Good to use |
| | 4 | D | 1 | White net | 0.1 | ○ | ⊙ | Optimum |
| | 5 | B | 1 | White net II | 0.1 | ○ | ○ | Good to use |
| | 6 | B | 1 | Non-woven fabric of polyester | 0.15 | ○ | ○ | Good to use |
| Comparative | 1 | E | 1 | White net | 0.1 | ○ | X | Not usable |
| Examples | 2 | F | 1 | White net | 0.1 | Not manufacturable | | Not usable |
| | 3 | B | 3 | White net | 0.1 | X | — | Not usable |
| | 4 | B | 2 | White net | 0.1 | Not manufacturable | | Not usable |
| | 5 | B | 1 | Stockinet | 0.1 | X | — | Not usable |

Figure 1:
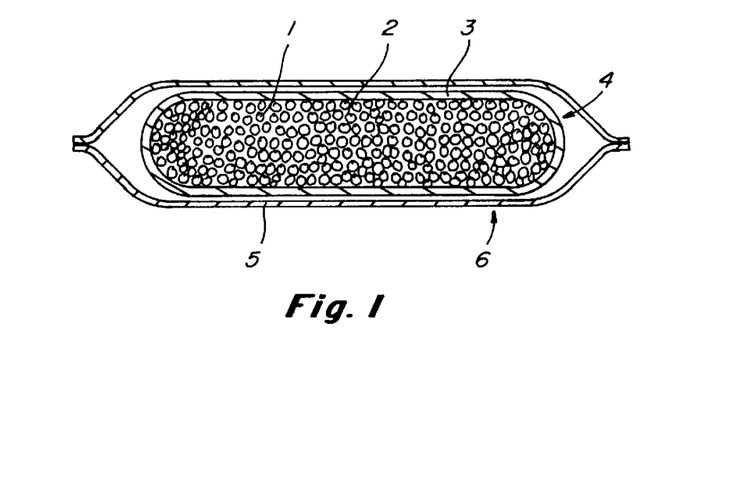
FIG. 1 is a sectional view showing an embodiment of the present invention.

FIG. 1 shows a sectional view of a forming material specimen to be preserved, wherein the reference numeral 1 denotes granulated materials coated with a moisture-curable urethane prepolymer 2 and housed in a bag-shaped water-permeable material container 3, thus forming a main forming material body 4. This main forming material body 4 is further enclosed in a bag-shaped moisture-impermeable material container 5, thus constituting a forming material 6.

Evaluation of Adhesion

Of the evaluation items, the adhesive strength between the cured urethane prepolymer and the water-permeable material was measured as follows:

(1) Preparation of the Test Specimens

The forming materials to be measured, a specimen preparation vessel and other necessary things such as scissors, a scale, etc. were manipulated in a glove box with its internal atmosphere replaced by nitrogen gas to open each forming material; the granulated materials coated with the moisture-curable urethane prepolymer were transferred into the specimen preparation vessel having dimensions of 200 mm×400 mm×20 mm until the vessel was filled up; and the surface of the thus transferred granulated materials was leveled by pushing a flat plate against it. Next, on the thus leveled surface of the granulated materials, a water-permeable material piece cut to a width of 25 mm×a length of 300 mm was placed, and, further, on this material piece, a stainless steel plate having a width of 35 mm×a length of 125 mm×a thickness of 2 mm was put, and in addition, a weight was added so that the load applied could become 165 g; and then the whole was taken out from the glove box. A sufficient amount of refined water at 20° C. was used (the pure water being allowed to run away from the lower side of the specimen preparation vessel) to cure the forming material. Thereafter, the whole was left to stand in a room at a room temperature of 20° C. to 25° C. and a relative humidity of 40% to 65% for 2 hours, and then the weight and the stainless steel plate were removed, thus preparing the specimen.

(2) Measuring Instrument and Measurement and the Result Thereof.

In a room under the environmental condition that the temperature was 23±2° C. and the relative humidity was 65±5%, three specimens were measured at a pulling rate of 300 mm/min by the use of an autograph (AG-500D manufactured by Shimadzu Corporation) in accordance with the 180° peeling method conformed to the JIS Z02378.3. 1. The measured data were obtained in such a manner that the average value of the values at the points at which the zone between 15% and 85% after the start of the pulling was divided into four equal portions was obtained, and further, the average value pertaining to the three specimens was set as the adhesive strength. The results obtained are shown in Table 4.

Evaluation of Storage Stability

The measurement of the storage stability was carried out as follows: That is, after the forming material was preserved at a temperature of 40±2° C. for one month, the main forming material body (the water-permeable material wrapping up the granulated materials therein) was taken out from the moisture-impermeable material in a room at a temperature 20±2° C. and a relative moisture of 65±5%; and, by means of visual observation and the use of hands wearing rubber gloves made of latex, the measurer touched the water-permeable material to check the state of permeation, that is, whether or not the moisture-curable urethane prepolymer had migrated into the water-permeable material; and the results thus obtained are shown in Table 4, wherein the cases where no permeation at all was effected are indicated by the mark ⊙, the cases where permeation was somewhat effected are indicated by the mark ○, the cases where penetration was effected but without leakage are indicated by the mark Δ, and the cases where penetration was effected and leakage resulted are indicated by the mark X. Further, the main forming material body was immersed in water at 20° C. for 10 seconds and then pulled up, and the extra water content was removed, and then, after the main forming material body was left to stand for 30 minutes, it was checked as to how the main forming material body was cured; and thus, the cases where a sufficient curing strength was obtained are indicated by the mark ○, while the cases where no curing strength was obtained are indicated by the mark X. The results thus obtained are shown in Table 4.

That is, in the case of Embodiment 1, the viscosity of the moisture-curable urethane prepolymer was at the lower limit, but, in respect of the storage stability, the moisture-curable urethane prepolymer penetrated into the water-permeable material but not to such an extent as to leak; and thus, this embodiment was usable. In the case of Embodiment 2, the viscosity of the moisture-curable urethane prepolymer exhibited an optimum value; nothing was wrong in respect of the storage stability; and thus, Embodiment 2 was good to use. In the case of Embodiment 3, the viscosity of the moisture-curable urethane prepolymer exhibited the upper limit value, but nothing was wrong in respect of storage stability; and thus, Embodiment 3 was good to use too. In the case of Embodiment 4, a thixotropic agent was added to the moisture-curable urethane prepolymer, so that the storage stability was very good; and thus, Embodiment 4 was even better suited for actual use. In the case of Embodiment 5, the openings of the water-permeable material were smaller than the size of the granulated materials, so that they were not at all allowed to flow out; and, due to the use of water-permeable material with a good stretchability, Embodiment 5 was excellent in modeling properties and thus good to use. In the case of Embodiment 6, the degree of stretching or shrinkage of the water-permeable material was 15% or higher, so that Embodiment 6 was excellent in respect of its modeling properties and thus also good to use. In contrast, in the case of Comparative Example 1, the viscosity of the moisture-curable urethane prepolymer was below the lower limit; as for the storage stability, the moisture-curable urethane prepolymer penetrated into the water-permeable material and leaked; and thus, Comparative Example 1 was not usable. In the case of Comparative Example 2, the viscosity of the moisture-curable urethane prepolymer was so high that the manufacture of the final-stage forming material could not be made. In the case of Comparative Example 3, the granulated materials and the moisture-curable urethane prepolymer reacted with each other, so that Comparative Example 3 could not be used. In the case of Comparative Example 4, the size of the granulated materials was smaller than the openings of the water-permeable material, so that the granulated materials flowed out through the openings, and thus, Comparative Example 4 was unusable. In the case of Comparative Example 5, the water-permeable material and the moisture-curable urethane prepolymer reacted with each other, so that Comparative Example 5 was unusable.

EXAMPLE 1

Figure 2A:
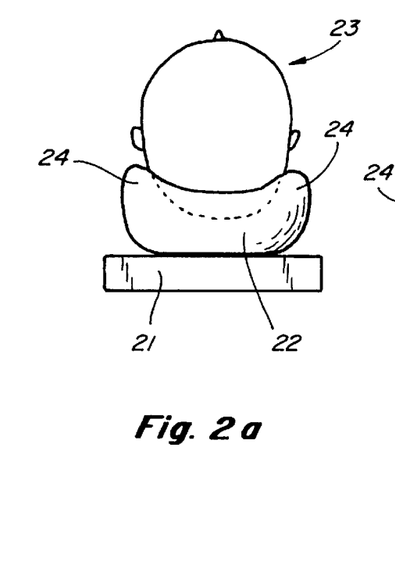
FIG. 2a is an end view of another embodiment of the present invention which is a fixing appliance for a head-neck portion, shown in supportive relation to a patient's head-neck portion.
Figure 2B:
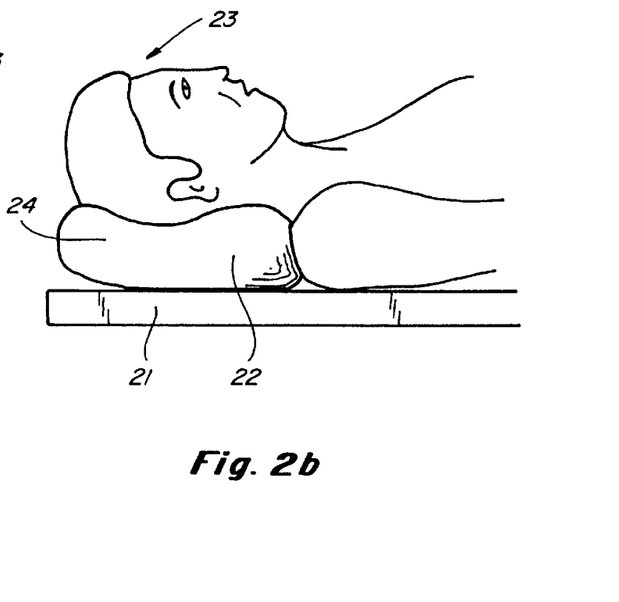
FIG. 2b is a side view of the fixing appliance of FIG. 2a, shown in supportive relation to the patient's head-neck portion.

An example of a method of forming or preparing a head-neck portion fixing appliance for radiation therapy, using the forming material according to the present invention will be described hereinbelow. A forming material of a size suited for a human head-neck portion (a forming material comprising the combination of component elements shown in connection with Embodiment 4 in Table 4; that is, a forming material composed in such a manner that about 2.5 liters of granulated materials coated with moisture-curable urethane prepolymer are enclosed in a water-permeable material container having a size of 200 mm×300 mm, and the whole is wrapped up in a moisture-impermeable material container), a water tank, and a bath towel are prepared; first, the moisture-impermeable material wrapper is opened; and the main forming material body is immersed in a water tank filled with water at 15 to 25° C., for 5 to 10 seconds; the main forming material body is pulled up to remove the excessive water therefrom; the main forming material body 22 is placed on the bath towel 21 laid down as shown in FIG. 2a and 2b; a patient is laid down in such a manner that his head-neck portion 23 is brought onto the main forming material body 22; portions 24 of the main forming material body which are protruding outside the head-neck portion 23 are manually pulled towards the head-neck portion 23; and after 5 to 10 minutes, the patient's head-neck portion is raised to allow the main forming material body 22 to dry, whereby a head-neck portion fixing appliance which has hardened in a shape having a depression perfectly coinciding with (the contour or profile of) the head-neck portion is obtained. This head-neck portion fixing appliance is lightweight and air-permeable and has suitable cushioning properties; and, by laying the patient down on this head-neck portion fixing appliance, his head-neck portion is always kept fixed at a fixed or exact position, so that an appropriate radiation therapy can be performed.

EXAMPLE 2

Next, an example of the formation of a fixing appliance for use as a seat made using a forming material according to the present invention will be described. A forming material of a size for a seat (a forming material comprising the combination of conditions shown as that for Embodiment 4 in Table 4; the forming material is composed in such a manner that about 12 liters of granulated materials coated with a moisture-curable urethane prepolymer are put and enclosed in a water-permeable material having a size of 400×800 (mm) and wrapped up with a moisture-impermeable material) is opened; the main forming material body is taken out, immersed in water at 15 to 20° C. for 5 to 10 seconds and then pulled up; and the excessive water is sufficiently removed; on a bath towel laid down in advance on a chair to which the forming material is to be applied, the main forming material body is set to an approximately uniform thickness; a patient or a person from whom a contour or profile model is to be formed is made to sit; those portions of the main forming material body which project out at both sides of his or her body are drawn up to his or her body sides; after the main forming material body ceases to be deformed in 5 to 10 minutes, the patient or person is made to stand up to allow the main forming material body to dry, whereby a fixing appliance for use as a seat which has been cured in a shape having a curved surface coinciding with the body shape of the patient or person is obtained. In the case of the thus formed fixing appliance for use as a seat, the patient or person is not tired even if he or she keeps sitting on the appliance for a long period of time, without suffering bed sores, and the appliance is air-permeable, so that a comfortable sense of seating can be obtained.

Effects of the Invention

According to the present invention, various kinds of appliances or equipment which have curved shapes accurately coinciding with the body shapes—which variously differ from person to person—of persons from whom contour or profile models are to be made can be made very easily and in a short time, and in addition, even if the forming material according to the present invention is preserved for a long period of time, it can be always effectively used without being deteriorated in quality at all. Furthermore, the appliances and equipment made by the use of the forming material according to the present invention are lightweight and highly air-permeable and have suitable cushioning properties, so that the appliances and equipment can be comfortably used and are easy to handle as well as excellent in durability.

Thus there has been shown and described several compositions and embodiments of a novel forming material which fulfill all of the objects and advantages set forth above. It will be apparent to those skilled in the art, however, that many changes, modifications, variations, and other uses and applications for the subject invention are possible. All such changes, modifications, variations, and other uses and applications which do not depart from the spirit and scope of the invention are deemed to be covered by the invention which is limited only by the claims which follow.

What is claimed is:

1. Forming material comprising:

a main forming material body hermetically enclosed in a moisture impermeable container, said main forming material body being comprised of a quantity of granulated material contained within a water-permeable container, said granulated material comprising individual granules coated with a moisture curable urethane prepolymer, said water-permeable container being treated with an agent for lowering its affinity with said moisture-curable urethane prepolymer selected from the group consisting of a fluorine agent, a paraffin agent, an alkyl chromic chloride agent, an alkylmethylpyridinium chloride agent, and an alkylethylene urea agent, and wherein the water-permeable material and the granulated material have a resultant adhesive force therebetween during curing of the urethane prepolymer of no more than about 0.5 kgf/25 mm.

2. Forming material according to claim 1, wherein the individual granules of the granulated material are no larger than about 10 mm in cross-section.

3. Forming material according to claim 2, wherein said individual granules are spherical in shape.

4. Forming material according to claim 3 wherein said granules comprise a foamed material.

5. A medical forming material made by a process comprising the steps of:

coating a plurality of individual granules with a moisture curable urethane prepolymer;

treating a water-permeable material with an agent for lowering affinity of the water-permeable material with the moisture curable urethane prepolymer selected from the group consisting of a fluorine agent, a paraffin agent, an alkyl chromic chloride agent, an alkymethylpyridium chloride agent, and an alkylethylene urea agent; and enclosing the coated granules within the treated water-permeable material to form a main forming material body, the water-permeable material and the granulated material having a resultant adhesive force therebetween during curing of the urethane prepolymer of no more than about 0.5 kgf/25 mm.

* * * * *

UNITED STATES PATENT AND TRADEMARK OFFICE
CERTIFICATE OF CORRECTION

PATENT NO. : 6,027,777
DATED : February 22, 2000
INVENTOR(S) : Hiroyuki Hirano, et al.

It is certified that error appears in the above-identified patent and that said Letters Patent is hereby corrected as shown below:

Col. 1, line 20, "fixing-and" should be --fixing and--.

Col. 6, line 20, "yarn/inch" should be --yarns/inch--.

Col. 18, lines 11-12, "alkymeth-ylpyridium" should be --alkylmeth-ylpyridium--.

Signed and Sealed this

Twenty-seventh Day of February, 2001

Attest:

NICHOLAS P. GODICI

Attesting Officer

Acting Director of the United States Patent and Trademark Office